(12) United States Patent
Poelstra et al.

(10) Patent No.: US 6,290,952 B1
(45) Date of Patent: Sep. 18, 2001

(54) METHOD OF DEPHOSPHORYLATING AN ENDOTOXIN IN VIVO WITH ALKALINE PHOSPHATASE

(75) Inventors: Klaas Poelstra, Buitenpost; Machiel Josephus Hardonk, Groningen; Winston Willem Bakker, Woltersum; Dirk KLaas Fokke Meijer, Groningen, all of (NL)

(73) Assignee: Rijksuniversiteit Groningen, Groningen (NL)

( * ) Notice: Subject to any disclaimer, the term of this patent is extended or adjusted under 35 U.S.C. 154(b) by 0 days.

(21) Appl. No.: 08/596,297

(22) PCT Filed: Aug. 10, 1994

(86) PCT No.: PCT/NL94/00189

§ 371 Date: Apr. 10, 1996

§ 102(e) Date: Apr. 10, 1996

(87) PCT Pub. No.: WO95/05456

PCT Pub. Date: Feb. 23, 1995

(30) Foreign Application Priority Data

Aug. 13, 1993 (WO) ................... PCT/NL93/00171

(51) Int. Cl.[7] .................. A61K 38/45; A61K 38/54; A61K 48/00; C12N 9/00
(52) U.S. Cl. ............... 424/94.2; 424/94.3; 424/94.5; 435/455; 435/458; 435/194; 514/44; 536/23.2
(58) Field of Search ................ 424/94.5, 241.2, 424/94.3; 435/182, 183, 194, 455, 458; 514/44; 536/23.2

(56) References Cited

U.S. PATENT DOCUMENTS

| | | | |
|---|---|---|---|
| 4,166,766 | * | 9/1979 | Metzenberg et al. . |
| 4,235,871 | * | 11/1980 | Papahadjopoulos et al. . |
| 4,378,352 | * | 3/1983 | Kimchi et al. . |
| 4,409,332 | * | 10/1983 | Jefferies et al. . |
| 4,480,041 | * | 10/1984 | Myles et al. . |
| 4,720,458 | * | 1/1988 | Sullivan et al. . |
| 4,782,016 | * | 11/1988 | Norton . |
| 4,861,597 | * | 8/1989 | Kida et al. . |
| 4,873,035 | * | 10/1989 | Wong . |
| 4,975,278 | * | 12/1990 | Senter et al. . |
| 5,017,501 | * | 5/1991 | Wong . |
| 5,124,253 | * | 6/1992 | Foulds et al. . |
| 5,248,590 | * | 9/1993 | Rutner et al. . |
| 5,252,336 | * | 10/1993 | Iga et al. . |
| 5,413,924 | * | 5/1995 | Kosak et al. . |

OTHER PUBLICATIONS

Kihn et al. American Journal of Clinical Pathology, 1991 Oct. vol. 96, No. 4, p. 470–478.*

Kim et al. Journal of Immunological Methods, vol. 159. Feb. 26,1993. p. 101–106.*

Urban et al. Infection and Immunity, vol. 58, No. 11, Nov. 1990, p3645–3652.*

* cited by examiner

Primary Examiner—Phuong T. Bui
(74) Attorney, Agent, or Firm—Fitch, Even, Tabin & Flannery

(57) ABSTRACT

The invention relates to pharmaceutical compositions suitable for treating or curing clinical complications mediated by endotoxin, including sepsis. The compositions contain components suitable for detoxifying endotoxin rendering it less deleterious to mammals such as humans, in particular to patients with reduced host-defence resistance. The invention also relates to pharmaceutical compositions suitable for stimulating bone formation, e.g. for mending broken bone or for prophylaxis or therapy of metabolic bone diseases such as osteoporosis and osteomalacia and pharmaceutical compositions for decreasing or inhibiting undesired bone formation. The pharmaceutical compositions according to the invention are directed at modulating phosphatase activity in vivo.

5 Claims, 9 Drawing Sheets

METHOD OF DEPHOSPHORYLATING AN ENDOTOXIN IN VIVO WITH ALKALINE PHOSPHATASE

This application claims benefit of international PCT/NL94/00189, filed Aug. 10, 1994.

FIELD OF THE INVENTION

The invention relates to pharmaceutical compositions suitable for treating or curing clinical complications induced by infections with Gram-negative bacteria, including sepsis. In particular the invention is directed at systemically applicable compositions. The compositions contain components suitable for detoxifying bacterial-wall derived lipopolysaccharides (also known as endotoxins) rendering these products less deleterious to mammals such as humans, in particular to patients with sepsis, optionally in combination with reduced host-defence resistance, i.e. after organ transplantations, during leucopenia (ref. 1) associated with cancer or chemotherapeutic treatment of cancer or during AIDS and AIDS-related diseases (ref. 2).

The invention also relates to pharmaceutical compositions suitable for stimulating bone formation, e.g. for mending broken bone or for prophylaxis or therapy of metabolic bone diseases such as osteoporosis and osteomalacia and also pharmaceutical compositions for decreasing or inhibiting undesired bone formation.

BACKGROUND INFORMATION

Endotoxin is a negatively charged lipopolysaccharide present in the capsule of Gram-negative bacteria (ref. 3). Endotoxins are complexes of phospholipid (lipid A) and polysaccharide. The endotoxins produced by different bacteria differ in their antigenicity but they all have the same biological effects which are mainly due to lipid A. For the purposes of this description the term endotoxin also comprises enterotoxins. In addition to the negatively charged sugar moieties, an endotoxin contains two phosphate groups which are essential for its toxicity (ref. 3, 4).

Although it is an ubiquitous molecule in the external environment as well as in the gastro-intestinal tract of many species, an endotoxin can be extremely deleterious to these species once it leaves the gastro-intestinal tract e.g causing sepsis and inflammation such as in an abcess even in amounts as low as 10 picogrammes. Yet so far, no important endotoxin detoxifying mechanism has been found in vivo (ref. 5).

Endotoxin is known to induce serious even lethal complications (ref. 5 and 6). In fact, despite the use of antibiotics, this bacterial product is the major cause of death in intensive-care units in Western society.

There are numerous different endotoxins produced by various microorganisms and consequently the actions of endotoxin in vivo are numerous as are the ways it can enter the organism. The symptoms associated with Gram negative infections therefore also vary widely among patients (ref. 7). These symptoms may be further complicated by septic shock of which hypotension, peripheral vasodilation and diffuse intravascular coagulation are the main characteristics (ref. 8). Subsequently organs such as heart (acute heart failure), lungs (adult respiratory distress syndrome). kidney (acute tubular necrosis) and brain may be affected (ref. 8). Endotoxin mediated pathology also comprises the syndrome of multiple organ failure and any other syndrome generally accepted in the art to be directly or indirectly caused by endotoxin.

To date, antibodies directed against endotoxin are the only endotoxin detoxifying proteins known to reduce toxicity irreversibly, but the clinical value of these antibodies remains to be established. Other substances which are able to bind endotoxin, such as lipopolysaccharide binding protein and high density lipoproteins (HDL) (ref. 9), exhibit the major drawback of forming reversible complexes in vivo. Upon dissociation of these complexes, the native (toxic) molecule is produced again. Furthermore although the detoxifying activity of plasma has been noted for some time (ref. 10) efforts to isolate or characterise the substance(s) responsible for this activity have not been successful. Other experimental approaches to treat sepsis include the application of preparations which antagonize the activities of cytokines (e.g. TNF-$\alpha$), which are important mediators of endotoxin-induced shock, aggravating the effects of endotoxin in vivo. A major disadvantage of this approach is that these preparations do not detoxify the causative agent but rather block one of the reactions of the body to this toxin. In addition, antagonizing naturally occurring cytokines may cause multiple side effects.

Alkaline phosphatase (EC 3.1.3.1) is a common enzyme present in many species, including man and has been studied extensively. The DNA sequence encoding alkaline phosphatase has even been obtained, but so far no commercial exploitation thereof has occurred. Although the enzyme is routinely applied as antibody label or as a marker for liver and neutrophil function, it's biological relevance is still unknown. Recombinant alkaline phosphatase enzymes with improved specific activity used as indicator reagents are disclosed, e.g. in EP-A-0 441 252. This patent application however mentions nothing regarding anti-endotoxin activity or bone formation of alkaline phosphatase. The cited European patent application describes a number of derivatives in which one amino acid differs from the wild type. The substituents include replacement of Thr 100 by Val or Ile, replacement of Lys 328 by Arg, replacement of Val 99 by Ala, replacement of Thr 107 by Val, replacement of Asp 101 by Ser, replacement of Val 377 by Ala and replacement of Ser 115 by Gly as well as replacement of Ala 103 by Asp. Other derivatives described in the cited patent application are derivatives with M maleimidobenzoyl-N-hydroxysuccinimide ester for carrying out a sandwich EIA and a thiolated mutant of alkaline phosphatase which can be derived through use of succinimidyl-4-N-maleimidomethyl-1-thicapramide cyclohexanecarboxylate. Of all these derivatives no mention is made of the charge carried by the alkaline phosphatase derivative. It is pointed out that all the mentioned derivatives with the exception of the replacement of Ala 103 by Asp have been calculated by us as resulting in a more positive netto charge or an equal netto charge in comparison to the corresponding native alkaline phosphatase.

Alkaline phosphatase is a membrane-bound ecto-enzyme which is known to dephosphorylate extracellular molecules. The enzyme is present in many organs, including intestine, kidney, osteoblasts and neutrophils (ref. 11, 12 and 13). in vitro, it exhibits a pH optimum of approximately 10.5. (ref. 12). This extremely high pH optimum has hampered recognition of its biological relevance (ref. 12–14), because it was felt that this pH level does not occur in biological tissues of the intact organism.

In a number of publications a derivative of alkaline phosphatase and collagen, in particular fibrillar collagen is described. Nothing is mentioned about the netto negative charge of such a derivative, however, we have calculated that the netto charge is positive in comparison to a non-derivatized alkaline phosphatase.

In U.S. Pat. No. 4,409,332 (1983) collagen sutures derivatized with alkaline phosphatase are described as reducing the inflammatory characteristics of collagen. The collagen induced inflammation is not an inflammatory reaction due to endotoxins, it is an inflammation that is generally caused by damage of tissue that has occurred, by the fact that collagen is a heterologous protein which is foreign to the body and by the fact that collagen always induces coagulation in vivo which can subsequently activate inflammatory cells in a number of manners. An inflammation due to infections of the wound is not likely as the authors themselves frequently state that they worked in a sterile environment, using sterile solutions. A person skilled in the art cannot derive from this cited patent publication how alkaline phosphatase coupled to collagen can inhibit the inflammation usually caused by collagen. A number of manners can however be postulated such as, for example by protection of antigens for cells of the specific immunoreaction, thereby prohibiting recognition or by binding positively charged mediators of the non-specific immune reaction as alkaline phosphatase contains negatively charged sugar groups. Another possibility is inhibition of the coagulation cascade by masking collagen or de-phosphorilation of mediators, such as ATP, ADP and platelet activating factor or by binding of positively charged mediators and cofactors.

In the cited document it is stated that even though the hydrolysis functions of outline phosphatase have intensively been studied for more than 50 years no clear image has arisen concerning the value of the enzyme to the organism. In summary the in vivo activity of alkaline phosphatase is not clear. No link is made in the cited document between alkaline phosphatase and bone formation or anti-endotoxin activity. No theoretical background is given to the anti-inflammatory activity of the coupling of alkaline phosphatase to collagen. It is in fact questionable whether a person skilled in the art would even attribute the anti-inflammatory activity to the presence of alkaline phosphatase or whether the fact that specific groups of collagen are protected by the presence of a random derivative provides the anti-inflammatory action. This can be derived from the fact that it is described that the use of cross-linking agent, such as glutaraldehyde or other cross-linking means appears to increase the anti-inflammatory characteristics of the material.

In U.S. Pat. No. 4,394,370 an anti-inflammatory complex of collagen and BMP is described as well as the use thereof in the healing of broken bones, which is further elucidated in U.S. Pat. No. 4,409,332. U.S. Pat. No. 4,394,370 describes the use of reconstituted collagen and dimineralized bone particles or reconstituted collagen and a solubilized bone morphogenetic protein, fabricated in a sponge for in vivo implantation in osseous defects. Both demineralized bone particles and bone morphogenetic protein have demonstrated the ability to induce the formation of osseous tissue in animal and human experiments. Reconstituted collagen conjugate is highly biocompatible and can be fabricated in a variety of configurations. This material can be used as a, grafting implant in plastic and reconstructive surgery, periodontal bone grafting and in endodontic procedures. The structural durability is enhanced by cross-linking with glutaraldehyde, which is also used to sterilize and disinfect the collagen conjugate prior to implantation. It is stated that the soluble factor from demineralized bone, bone morphogenetic protein is osteo inductive and it is also known that the demineralized bone is also condusive to osteogenesis. The use of alkaline phosphatase coupled to BMP and collagen as disclosed in U.S. Pat. No. 4,394,370 is not directed specifically at a bone formation increasing activity of alkaline phosphatase as such but more the fact that alkaline phosphatase linked to collagen has a less inflammatory character than non-derivatized collagen. U.S. Pat. No. 4,394,370 is in particular directed at collagen BMP conjugate sponges and the use of alkaline phosphatase conjugated to such a sponge is merely one of a number of embodiments of BPM-collagen uses and as such is not directed at the same invention as the subject patent application namely the in vivo activity of phosphatase as such or derivatives thereof amongst others for increased bone formation. In U.S. Pat. No. 4,394,370 no mention is made of the anti-endotoxin activity of alkaline phosphatase.

WO 93/00935 describes that the possible role of the enzyme alkaline phosphatase in promoting the calcification of bone has been postulated for many years. However that the relevance of such in vitro mineralization studies to the situation in vivo has been questioned, particularly in view of the relatively high concentrations of phosphate esters used in the in vitro studies and also because the rate of hydrolysis of the phosphate esters and physiological pH levels would be expected to be too low to be relevant to the process of mineralization. In the cited patent application Beertsen et al. describe that combination of a biocompatible carrier material, preferably one which can mineralize to some degree itself, such as fibrillar collagen with a quantity of a phosphatase enzyme will promote mineralization. Preferably the combination of alkaline phosphatase with the carrier is brought about by incubating the carrier with the enzyme in the presence of a coupling agent capable of covalently bonding with the carrier and with the enzyme. Suitable coupling agents are described as biotinavidin, glutaraldehyde and 1-ethyl-3-(3-dimethyl-aminopropyl) carbodiimide HCl. A particularly preferred coupling agent is known as succinimidyl-s-acetyl-thioacetate (SATA) in combination with maleimido hexanoyl-N-hydroxysuccinimide (MHS) wherein the carrier is incubated with SATA and the enzyme with the MHS. The products of these two incubation processes are combined and allowed to react to produce an implant material. The cited document describes that the coupling of alkaline phosphatase to collagen improves the osteogenesis when such a complex is placed in situ of the wound. The alkaline phosphatase is used in combination with a product already known to stimulate bone formation. No description is given of use of alkaline phosphatase as such or as a derivative with a particular altered charge. It is pointed out that a derivative of alkaline phosphatase with fibrillar collagen has an increased positive charge in comparison to non-derivatized alkaline phosphatase. A derivative of alkaline phosphatase with fibrillar collagen is not suitable for systemic application as fibrillar collagen induces intravascular platelet activation leading to embolisms. Therefore, a complex of fibrillar collagen and alkaline phosphatase could not be used in a method for treating osteoporosis or osteomalacia or any other bone defect which requires systemic application. It can only be used when immobilized in situ at the location of a wound.

DESCRIPTION OF THE INVENTION

The subject of the present invention is based on our finding that alkaline phosphatase as such is endowed with phosphatase activity regulating certain vital body functions, even at physiological pH levels, i.e. in vivo without having to be derivatized.

The basis for this insight was provided by the idea that at the molecular level in vivo, an alkaline micro-environment could present itself differently from aqueous solutions in vitro. In vivo negatively charged molecules may act as weak bases by their ability to bind H⁺. Consequently these anions induce a local increase in the pH level thereby providing a micro environment with a pH value sufficient for the alkaline phosphatase to function as phosphatase.

The addition of negative charges can be provided in vivo in three different ways: addition of net negatively charged substrates to the enzyme, secondly providing the phosphatase with a membrane carrier with negative charges and thirdly by changing the ionization of charged groups in the protein itself and/or introducing negatively charged moieties in the protein backbone or removing potentially positively charged groups in the protein.

These different mechanisms either alone or in combination may explain the unusual high pH optimum of the enzyme in vitro.

Similar considerations could be applicable to other types of phosphatases.

Another aspect of the present invention is based on the even more specific finding that alkaline phosphatase as such is also endowed with endotoxin detoxifying activity, even at physiological pH levels.

Endotoxin having negatively charged moieties can thus for example supply negatively charged residues necessary in the alkaline phosphatase's micro environment. In this way, this ubiquitous enzyme can provide protection in vivo against endotoxin, the ubiquitous product of Gram negative bacteria.

The use of enzyme preparations to detoxify endotoxin itself has the advantage that treatment of the disease in the early stage is possible and has the further advantage of irreversibly reducing toxicity of the endotoxin. In addition as activity of enzymes is substrate specific the side-effects of using an enzyme such as alkaline phosphatase are limited.

The phosphate groups in the lipid A moiety of endotoxin determine the toxicity of this bacterial component. Whilst dephosphorylated lipid A molecules retain some of their immunostimulatory activities it thus becomes possible to make a vaccine.

A vaccine for preventing pathology mediated by endotoxins of gram negative bacteria, said vaccine comprising phosphatase as such or a derivative of phosphatase, said derivative having phosphatase activity as active component and any adjuvant commonly used in a vaccine is an embodiment of the subject invention. Any type of derivative generally acceptable in the field of vaccines can be used.

Yet a further aspect of the invention is directed at the use of alkaline phosphatase as such as active component in a pharmaceutical composition for treatment or prophylaxis requiring increasing bone formation e.g. for stimulating the mending of broken bones or in particular for treatment and/or prophylaxis of metabolic bone diseases such as osteoporosis and osteomalacia. The negative charges necessary for optimal alkaline phosphatase activity in vivo may not only be provided by the substrate but also by the micro-environment, or both.

In bone for instance, alkaline phosphatase is found in an extracellular environment rich in glycosaminoglycan (GAG)-chains, osteopontin, osteocalcin and bone sialo protein. All of these molecules are particularly characterized by their high content of negatively charged residues (ref. 15). To date, the role for alkaline phosphatase in bone formation is obscure. However, its significance may be reflected by the fact that the enzyme is present at sites of bone formation (e.g. in the extracellular space between two sites of a bone fracture (ref. 16 & personal observations). Moreover, a disease like hypophosphatasemia, characterized by low levels of alkaline phosphatase activity in bone and serum is associated with skeletal deformations (ref. 17).

Again, the substrate for alkaline phosphatase is unknown, mainly because of the unphysiological high pH optimum of the enzyme using various substrates. However, in the light of our idea it is easily conceivable that when a given phosphorylated substrate becomes attached to strongly negative molecules, the proper micro-environment is created. In such a condition, alkaline phosphatase may express optimal activity at physiological pH levels, and dephosphorylate this substrate thereby contributing to the formation of insoluble calciumphosphate-complexes, an important constituent of bone matrices.

Alkaline phosphatase or a derivative thereof may locally dephosphorylate organic phosphate esters (of yet undefined nature) and thus contribute to the formation of calcium phosphate-complexes. In addition, since high concentrations of inorganic phosphate in the extracellular environment are necessary to create the optimal physico-chemical conditions for bone-mineralization (a high ionic strength facilitates precipitation of phosphate-complexes), plasma alkaline phosphatase or a derivative thereof activity may increase inorganic phosphate concentrations in blood and thus further contribute to the process of bone formation. Therefore, alkaline phosphatase or a derivative thereof apparently has a dual effect in vivo: it directly causes mineralization of the bone matrix and it further facilitates this process by causing supersaturation of the environment with phosphate.

Recent experimental data support this notion regarding the role of a derivative of alkaline phosphatase in vivo during bone formation. Sheets of collagen layers coated with an alkaline phosphatase derivative are rapidly mineralized when implanted subcutaneously in rats (ref. 32). The degree of mineralization depends on the amount of alkaline phosphatase derivative bound to the collagen implants, and on the serum levels of inorganic phosphate in these animals. Older female rats (35 weeks of age) showed lower serum levels of Pi and a lower degree of mineralization of the implants as compared to young male rats. In addition, dietary phosphate deprivation in normal mice leads to impaired bone formation (ref. 33). Also in vitro, mineralization of collagen sheets coated with the alkaline phosphatase derivative could be attenuated by reducing Pi concentrations in the medium.

Metabolic bone diseases such as osteoporosis and osteomalacia generally affect the elderly man. Conflicting reports exist as to the question whether serum alkaline phosphatase activity is increased, decreased or unchanged in elderly people (for a review see ref. 34). It is known that serum alkaline phosphatase activity may not reflect tissue-bound alkaline phosphatase activity adequately (ref. 34). In fact, several reports suggest a gradual decrease in alkaline phosphatase activity in for instance hepatic cells (ref. 35) intestina and leucocytes (ref. 36) with age. It may be speculated that metabolic bone diseases like osteoporosis and osteomalacia are characterized by an impaired activity of alkaline phosphatase or a derivative thereof in situ, caused either by a local lack of enzymes or by a reduced amount of negatively charged molecules within the micro-environment. The higher incidence of osteoporosis in the female population may also be explained by the notion that alkaline phosphatase or a derivative thereof is involved in the pathogenesis of this disease: the activity of alkaline phosphatase or a derivative thereof is, at least in women, regulated by hormones such as estradiol (ref. 37), as is also demonstrated by the rise in serum alkaline phosphatase activity during pregnancy (ref. 18). In the menopause this regulating system disintegrates.

It is conceivable that a lower serum alkaline phosphatase activity causes a lower concentration of Pi in blood and that this condition can be reversed by administration of (alkaline) phosphatase or a derivative thereof with (alkaline) phosphatase activity with a long circulating half-life. In the light of the above mentioned, bone mineralization may be further enhanced by coupling (alkaline) phosphatase to negatively charged molecules and/or by increasing the intrinsic anionic charge of (alkaline) phosphatase. Administration of (alkaline) phosphatase as such, or stimulating (endogenous (alkaline)) phosphatase activity and/or production, may therefore be beneficial to patients with metabolic bone diseases such as osteoporosis or osteomalacia. Systemic application of (alkaline) phosphatase as such as active component of a pharmaceutical composition to persons with (multiple) bone fractures and a pharmaceutical composition comprising (alkaline) phosphatase as such as active component also fall within the scope of the present invention. In addition, inhibition of (alkaline) phosphatase activity may be an option for therapy in patients with malignancies characterized by excessive bone-formation, such as osteosarcoma, or secondary tumours derived from metastatic carcinoma's. The high alkaline phosphatase activity found in osteosarcoma tissue (ref. 19) may therefore not only be a diagnostic marker for increased bone formation but an entrance for therapeutic intervention as well.

The subject invention is therefore also directed at a method of treatment of pathology associated with rapid bone formation such as osteosarcoma, said method comprising decreasing or inhibiting alkaline phosphatase activity, preferably in a target specific manner i.e. at the location where said pathology occurs. The decrease in phosphatase activity can be brought about e.g. by lowering formation of phosphatase or by competitively binding phosphatase preventing it's dephosphorylation. A pharmaceutical composition comprising at least one substance capable of decreasing or inhibiting phosphatase activity and/or the concentration of (alkaline) phosphatase (activity), said substance preferably being targeted to act at a location where undesired bone formation is to be prevented also falls within the scope of the invention.

A pharmaceutical composition according to the invention is preferably non-toxic in the circulatory system and thus systemically acceptable and applicable. This allows the use against endotoxin and metabolic bone diseases and also eliminates the need for surgery in some cases where broken bones need mending.

To test the hypothesis that alkaline phosphatase is a protective enzyme of the host-defence system by its ability to detoxify lipopolysaccharides, we investigated whether alkaline phosphatase is able to dephosphorylate endotoxin of *Escherichia coli* at physiological pH levels. Alkaline phosphatase activity was explored in 4% formalin-fixed cryostat sections (4 μm) of intestine, kidney and spleen according to standard histochemical methods at alkaline (ref. 20) and physiological pH levels (ref. 21), using either the conventional substrate β-glycerophosphate (6.0 mg/ml) or endotoxin from *Escherichia coli* (0.55 mg/ml; serotype 0.55:B5, Sigma Chemical Co, St.Louis, U.S.A.). At alkaline pH level, the histochemical method of Gomori (ref. 20) was applied, whereas the method of Wachstein and Meisel (ref. 21) was used at the lower pH level. Sections were incubated with substrate for one hour at 37° C. At pH 7.4 and 9.0, phosphate precipitates, indicating enzyme activity, were found in intestine and kidney sections when endotoxin was used as substrate (FIG. 1). In the spleen, strong positive cells scattered throughout the red pulpa were found. Distribution of reaction product was identical for both substrates. All sections incubated without substrate were completely devoid of reaction product. In addition, the selective alkaline phosphatase inhibitor levamisole (1.0 mM) (ref. 20) completely inhibited phosphate release from endotoxin in kidney sections, whereas in intestine sections this activity was attenuated by the well known inhibitor of intestinal alkaline phosphatase, L-phenylalanine (5 mM) (ref. 22), but not by the stereoisomer D-phenylalanine (5 mM). Thus, both distribution of enzyme activity in various organs, as well as results obtained with selective inhibitors demonstrate that endotoxin is dephosphorylated by alkaline phosphatase at physiological pH levels.

The pH optimum of alkaline phosphatase activity was studied in a more quantitative way using tubular brushborder fragments of the rat kidney. This particular enzyme preparation has the advantage that it can be studied in association with the plasma membrane. Moreover, it can be completely inhibited by levamisole. Preparations of tubular brushborder fragments (isolated from the cortex of PVG rat kidneys using a sieve of 180 mesh and rinsed in 0.9% saline) which contained 12 μg protein (specific phosphatase activity: 86 U/mg, as assessed at pH 9.8) were added to 250 μl 2-amino-2-methyl-1,3-propanediol buffer of various pH levels. The buffer contained either endotoxin from *E. coli* (1.25 mg/ml) or paranitrophenolphosphate (0.5 mg/ml; pNPP). 2 mM $MgCl_2$ was added shortly before the start of the incubation period. After one hour incubation at 37° C., inorganic phosphate concentrations were assessed according to the method of Chandrarajan (ref. 23). With the conventional substrate pNPP a steady increase in phosphate release along with the pH was observed (FIG. 2, upper left corner); however, when endotoxin was applied as substrate, enzyme activity reached a maximum at pH 8.8 and remained stable at this level. Endotoxin- as well as pNPP-dephosphorylation was inhibited by the alkaline phosphatase inhibitor levamisole (0.2 mM). Activity at high pH levels was not hampered by de-acetylation of fatty acyl chains of endotoxin occurring at alkaline conditions (ref. 24), since one hour pre-incubation of endotoxin at pH 9.8 did not inhibit dephosphorylation at pH 7.4 as tested histochemically. Thus, in contrast to the high pH optimum found with the substrate pNPP, alkaline phosphatase reaches maximal activity at a less extreme pH level when endotoxin is used as substrate. It may be speculated that the pH optimum is even lower when the enzyme is studied in vivo within its proper micro environment comprising the necessary additional negative charges to mimic the alkaline pH optimum observed in vitro.

To study the effect of alkaline phosphatase upon endotoxin toxicity, Limulus assays were performed. This Litulus assay is the standard method to assess endotoxin concentrations in vitro, based upon toxicity of the molecule towards the horseshoe crab *Limulus polyphemus* (ref. 25). Endotoxin (2.0 ng/ml) was incubated for one hour at 37° C. in RPMI-1640 buffer (pH 7.6), together with tubular fragments (0.8 μg protein/ml, specific phosphatase activity 86 U/mg). Control samples lacked either endotoxin or tubular brushborder fragments. Subsequently the Limulus assay was performed. Results show a significant reduction in endotoxin concentrations as measurable by this method in suspensions containing endotoxin and alkaline phosphatase activity, as compared to suspensions containing equal amounts of endotoxin without the enzyme (Table 1). It can be concluded that alkaline phosphatase is able to attenuate the toxicity of endotoxin molecules at physiological pH levels, as assessed in vitro.

A further method at which the invention is a method for rendering a substance free of toxic effects of endotoxin comprising subjecting the product to the phosphatase activity of phosphatase, e.g. alkaline phosphatase or a derivative of phosphatase having phosphatase activity. Such a derivative can for example be a derivative as described herein. The substance to be detoxified must be subjected to the presence of the phosphatase activity during a sufficient length of time to detoxify any endotoxin present. A person skilled in the art will be able to ascertain what length of time this can suitably be without undue experimentation.

TABLE 1

Endotoxin concentrations as measured by the Limulus assay with and without pre-treatment with alkaline phosphatase

| sample | [endotoxin] pg/ml |
| --- | --- |
| Endotoxin | 34.0 ± 13.00 |
| Endotoxin + alkaline phosphatase | <0.05 ± 0 |
| Buffer | 11.3 ± 9.8 |

The toxicity of endotoxin treated with alkaline phosphatase was also studied in vivo, taking advantage of the fact that local inflammation following two successive endotoxin injections (the local Shwartzman-reaction (ref. 26)) can readily be quantified. If the detoxifying hypothesis were valid, this inflammatory reaction should be reduced after administration of endotoxin preparations pre-treated with alkaline phosphatase. Therefore, we elicited a local intradermal Shwartzman-reaction and treated the second endotoxin dose with tubular brushborder fragments at physiological pH. Influx of oxygen free radical producing cells, an important feature of the Shwartzman-reaction, was subsequently examined histochemically. Thus, the Shwartzman-reaction was elicited by two successive injections of endotoxin (from $E.$ $coli$ 055:B5) divided by 20 hours in female PVG rats (200 g). The first endotoxin injection (1 mg/kg b.w.) was administered intravenously, whereas the second injection consisted of an intradermal administration of a mixture of 70 µl RPMI 1640-medium (pH 7.6) supplemented with 2 mM $MgSO_4$ and 40 µg endotoxin (E) or $MgSO_4$ alone (C). Prior to injection, media were incubated (1 hour, 37° C.) with 6 µg tubular brushborder fragments containing 86 U/mg alkaline phosphatase activity (A), with or without the alkaline phosphatase inhibitor levamisole (L; final concentration 1.0 mM). Control media were supplemented with saline (S) and lacked either endotoxin, or alkaline phosphatase, or both. Two hours after the intradermal injections, dermal sites were analyzed for influx of oxygen free radical producing cells, demonstrated histochemically with 3,3'-diaminobenzidine (DAB) at the light microscopical level (ref. 27). A significant influx of oxygen free radical producing cells was observed in dermal sites injected with untreated endotoxin as compared to controls (E/S versus C/S p<0.01, Wilcoxon; FIG. 4). This inflammatory response was attenuated at dermal sites injected with endotoxin pretreated with tubular brushborder fragments (E/S versus E/A, p<0.05, Wilcoxon), whereas endotoxin pretreated with tubular fragments plus levamisole displayed increased pro-inflammatory activity as compared to endotoxin pretreated with tubular fragments alone (E/A versus E/A/L, p<0.025, Wilcoxon). Each test was performed in duplicate on the same rat and results are expressed as the arithmetic means (+/−SD) of 6 rats. These data demonstrate that endotoxin treated with alkaline phosphatase exhibits reduced toxicity in vivo and that alkaline phosphatase may be able to detoxify endotoxin in vivo.

To examine the contribution of endogenous alkaline phosphatase activity in the endotoxin detoxification in vivo, we assessed the effect of levamisole upon endotoxin-sensitivity in rats, a species relatively resistant to Gram-negative lipopolysaccharides. Female PVG rats, 6 months of age, received the alkaline phosphatase inhibitor levamisole (Sigma Chemical Co, St.Louis, USA) intraperitoneally (10 mg/kg b.w.), or saline at t=−24 and t=−1 hour. At t=0, rats received an i.v. challenge of 0.5 mg endotoxin, and blood was collected immediately prior to and at t=3, 6, 24 and 48 hours after this injection.

Serum glutamate-pyruvate transaminase activity, reflecting liver damage (an important pathogenic factor in endotoxin-induced death) was assessed in these samples according to the method of Wroblewski and LaDue. Results showed no change in serum transaminase activity after treatment with levamisole alone as compared to saline treated rats whereas an increase was found after the endotoxin challenge (FIG. 5). However, in contrast to the minor increase observed in rats receiving only endotoxin, rats pre-treated with levamisole displayed a very strong increment in serum transaminase activity (p<0.001), demonstrating the involvement of endogenous alkaline phosphatase activity in the endotoxin-detoxifying activity of rats in vivo.

The detoxifying activity of alkaline phosphatase was also studied in an experimental model of septic shock in rats and mice. Thus, rats received an intraperitoneal injection of $1.0 \times 10^{10}$ colony forming units (CFU) of a well characterized strain of $Escherichia$ $coli$ bacteria (ATCC 25922) whereas mice received $0.2 \times 10^{10}$ CFU. Inoculation of this dose leads to the full blown septic shock syndrome, characterized by thrombocytopenia. leucopenia, impaired liver function and reduced (rectal) body temperature, within approximately 6 hours.

Most rats, being relatively resistant to endotoxin, survived the injection of $E.$ $coli$ bacteria (FIG. 7A). However, in combination with the alkaline phosphatase-inhibitor levamisole (50 mg/kg b.w. administered subcutaneously 2 hours prior to the bacteria) inoculation of Gram-negative bacteria was lethal. Nine out of ten rats died with clinical symptoms of shock. Serum levels of alkaline phosphatase activity in rats treated with Levamisole were reduced by 50% six hours after the injection. Levamisole did not influence survival of rats which received a sublethal dose of Gram-positive bacteria; rats receiving 50 mg/kg b.w. Levamisole 2 hours before administration of $1.0 \times 10^{10}$ CFU $Staphylococcus$ $aureus$ nearly all survived (8 rats per group, FIG. 7B). This demonstrates that endogenous alkaline phosphatase activity in rats is involved in the resistance towards endotoxin of Gram-negative bacteria.

In contrast to rats, nine out of ten mice died from of dose of $0.2 \times 10^{10}$ CFU $E.$ $coli$ (FIG. 8). However, animals receiving a single intraperitoneal injection of 0.15 U purified human placental alkaline phosphatase 2 hours before the administration of bacteria all survived the inoculation of this lethal dose (n=10), alkaline phosphatase was extracted from human placenta with butanol (50% v/v) and purified using a diethylaminoethyl cellulose column and an affinity column (a CNBr-sepharose$^{4B}$ column with rabbit-anti-human-placental alkaline phosphatase antibodies coupled to it). Thus, alkaline phosphatase appears to be able to detoxify endotoxin in vivo and seems applicable for the treatment of endotoxic shock.

The circulating half-life of placental alkaline phosphatase is approximately 7 days in human blood (ref. 31). In rats human placental alkaline phosphatase is detectable in blood for approximately three days (personal observations), in contrast to intestinal alkaline phosphatase which has a circulating half-life of 7 1/2 minutes (ref. 28). Based on these data and based upon the results of studies in mice (see above), it can be concluded that placental alkaline phosphatase is particularly suitable to serve as an active component in a pharmaceutical composition, in particular a systemically applicable composition such as for the prevention of sepsis.

The anti-endotoxin activity being based on the dephosphorylating activity exhibited by alkaline phosphatase can naturally not be excluded for other phosphatases, in particular phosphatases with optimum pH in vitro at alkaline pH or derivatives of phosphatases having phosphatase activity. The subject invention is therefore directed at the use of a phosphatase as such or a derivative thereof having phosphatase activity as active component for the preparation of a pharmaceutical composition for prophylaxis or therapy of pathology mediated by endotoxin or by a derivative of endotoxin having endotoxic activity. A pharmaceutical composition comprising at least a phosphatase as such or a derivative thereof having phosphatase activity suitable for systemic application or comprising a vehicle capable of producing phosphatase as such or a derivative of phosphatase having phosphatase activity suitable for systemic application as active component, said phosphatase or said derivative having detoxifying activity for an endotoxin or for a derivative of endotoxin having endotoxic activity and further comprising a pharmaceutically acceptable carrier, falls within the scope of the invention. In particular a pharmaceutical composition comprising alkaline phosphatase as such or a derivative thereof having phosphatase activity or a vehicle capable of producing alkaline phosphatase as such forms a preferred embodiment of the invention. For use in a pharmaceutical composition the phosphatase must be obtainable in a substantially pure form. In general recombinant DNA techniques can provide a phosphatase suitable for use in a pharmaceutical composition according to the invention.

To date, four isozymes encoded by four distinct genes have been described. These include the intestinal form, the liver/bone/kidney-type (also present in neutrophils), the placenta-type, and the placental-like isozyme (present in germinal cells). Both the intestinal form and the liver/bone/kidney-type alkaline phosphatase exhibit endotoxin detoxifying activity, whereas there are no reasons to believe that the other isozymes of alkaline phosphatase are not able to degrade endotoxin. Therefore the subject invention comprises a pharmaceutical composition comprising any such isozyme. In particular an alkaline phosphatase of the placental type is suitable due to the long half life thereof in vivo.

The following case history illustrates the deleterious consequences of a reduced alkaline phosphatase activity in a mammal such as a human. A one year old female child suffered from recurrent endotoxaemia. These periods were accompanied with life-threatening symptoms of shock. Upon treatment, recovery was achieved, however, often followed by a relapse within a few weeks when endotoxaemia occurred again. In a period of 10 months, 12 relapses happened and finally the child died at the age of one year. The cause of death was diagnosed as septic shock induced by Gram-negative bacteria. The cause of the recurrent endotoxaemia itself was unknown. Our recent studies showed that in liver and spleen, alkaline phosphatase appeared normal, but enzyme activity was nearly absent in the ileum, an organ which normally expresses the highest enzyme activity of the human body. In the light of our finding, a reduced alkaline phosphatase activity in such a crucial organ, may explain the cause of death. It is easily conceivable that the lack of an endogenous detoxifying mechanism in the intestine results in recurrent endotoxaemia, considering the high content of E. coli in the intestinal lumen. Such a deficiency might be adequately treated according to the subject invention.

Retrospective studies in patients suffering from recurrent endotoxemia (without underlying complications such as malignancies or liver-diseases) showed that serum alkaline phosphatase or a derivative thereof activity correlates with the clinical condition. Thus, when sepsis occurred, invariably a strong decrease, in serum alkaline phosphatase or a derivative thereof activity could be measured, a phenomenon also found in rats, followed by an increase in alkaline phosphatase or a derivative thereof activity in serum within a few days. In a particular case, the inflammatory tissue was removed (partial ileum-resection) during a period of serious illness. This caused an immediate rise in serum alkaline phosphatase or a derivative thereof activity to normal levels. These observations point to an increased turn-over of the enzyme during Gram-negative bacterial infections and support the notion that alkaline phosphatase or a derivative thereof administration to patients with sepsis may be helpful.

A method for therapy or prophylaxis of pathology mediated by endotoxin or by a derivative of endotoxin having endotoxic activity comprising administering to a subject a therapeutic amount of a phosphatase or derivative of phosphatase having phosphatase activity therefore also falls within the scope of the invention. Derivatives with optimal activity around in vivo pH will be preferred. Use of phosphatase derivatives in a method for preparation of a pharmaceutical composition for prophylaxis of therapy of pathology mediated by endotoxin or a derivative of endotoxin naturally therefore also falls within the scope of the invention. An especial preference is expressed for systemically applicable derivatives as such derivatives can be applied in the bloodstream of the subject to be treated as already elucidated for phosphatase as such. For effectivity against Gram-negative bacterial infections the active component must preferably arrive at any location where a Gram-negative bacterium or it's endotoxin can be located.

Another aspect of the invention lies in the insight that in accordance with the Brønsted-Lowry classification of acids and bases, polyanions may act as weak bases since they are able to bind $H^+$. Thus extrapolating this to the fact that optimal functioning of proteins or polypeptides is often pH dependent and that in particular in vitro it has been illustrated that the incubation medium has to be alkaline for optimal activity of said proteins or polypeptides, in particular for alkaline phosphatase, we have concluded that in vivo polyanionic sites, for instance negatively charged sialoglycoproteins associated with cell membranes may meet the pH demands of such an enzyme or polypeptide.

Alkaline phosphatase is predominantly found in association with plasma-membranes. For example, neutrophils present the enzyme against the background of their negatively charged cell membrane instead of releasing it into the inflammatory micro-environment. For this reason it is felt that poly-anionic substrates could further contribute to favourable an ionic conditions in vivo for phosphatase activity of phosphatases and derivatives thereof normally having an optimum at an alkaline pH, in particular for phosphatase activity of alkaline phosphatase.

If negatively charged sugar moieties of endotoxin influence the pH optimum of this enzyme activity, polycations could be expected to interfere with this reaction. Therefore, we treated the substrates with the cations polyethyleneimine (PEI) or poly-L-lysin (Lys). Substrates were preincubated for 30 minutes with either 0.5% PEI, 0.75% poly-L-lysin or distilled water (C). Subsequently, incubations were carried out as described above and phosphate release was assessed. Both cations strongly affected dephosphorylation of endotoxin by neutralising the negative charges, whereas neither one of them significantly influenced pNPP degradation (FIG. 3). The profound effect of PEI upon endotoxin degradation may be caused by neutralisation of negative Charges whereas steric inhibition may also add to this effect. Interestingly, poly-L-lysin caused a shift of the pH optimum to a higher level, supporting the idea that negatively charged residues in the micro environment determine the pH optimum.

Additional support for the notion that negatively charged molecules in the micro-environment influence the pH optimum of alkaline phosphatase was also derived from experiments with intestinal enzymes. Histo-chemical assessment of the pH optimum of alkaline phosphatase in cryostat sections (4 μm) of rat intestine applying the method of Gomori with the substrate pNPP, revealed no significant change in staining intensity when the pH level of the incubation medium was varied from 7.8 to 9.8. However, alkaline phosphatase activity in serum, which is shown to be of intestinal origin, exhibits a pH optimum of 9.8 or higher. An important difference between intestinal alkaline phosphatase in situ and in serum is the sialoglycoprotein content thereof. Although the intestinal enzymes are embedded in sialated plasma membranes. serum alkaline phosphatase is not surrounded by these polyanions.

The subject invention is therefore also directed at a derivative of a phosphatase having phosphatase activity and comprising a net higher content of negatively charged moieties than the corresponding native phosphatase. In particular the invention is directed at such a derivative being derived from a phosphatase with an optimum at alkaline pH such as alkaline phosphatase.

A derivative of a phosphatase according to the invention comprising a higher content of negatively charged moieties can comprise a higher content of derivatized alkaline amino moieties than the corresponding native phosphatase. This can for example be achieved by said derivative comprising a higher content of negatively charged N-acetylneuraminic acid groups (=sialic acid groups) than the corresponding native phosphatase. Another possibility lies in the derivative comprising a higher content of negatively charged acid and/or a reduced number of basic moieties than the corresponding native phosphatase as such or in combination with the aforementioned embodiment. In yet another embodiment of the invention the derivative of phosphatase can comprise a phosphatase moiety connected to a negatively charged protein or polypeptide. A suitable example of such a negatively charged protein is a modified negatively charged albumin, e.g. a succinylated albumin. It is repeated that the disclosed derivatives of phosphatase of WO 93/00935, U.S. Pat. Nos. 4,394,370, 4,409,332 and EP-A-0441252 are not derivatives with an increased netto negative charge. The only more negatively charged derivative disclosed in said literature is the recombinant *E. coli* alkaline phosphatase with substitution of Ala 103 by Asp. In addition, none of the disclosed derivatives are systemically applicable. A person skilled in the art will know what type of derivatives are implied by the term systemically applicable. What is of particular interest are derivatives that can be used in oral dosage forms, or intravenous solutions or any medicinal dosage form such that the active components can enter the bloodstream. Toxic derivatives such as collagen derivatives are not acceptable.

In a further aspect of the invention a derivative of phosphatase can comprise at least one modification for increasing the half life of said derivative in vivo, e.g. by preventing binding to galactose receptors, said modification e.g. being located at the terminal galactose residue of a phosphatase such as alkaline phosphatase. It was already known that removal of e.g.serum alkaline phosphatase is mediated by hepatic galactose receptors (ref. 28) but no attempt to modify a substrate of such a receptor has been taught or suggested previously. The modification can e.g. be the result of an oxidation or reduction.

The invention not only covers the derivatives as such in the various embodiments described above but also comprises combinations of the various aspects of such embodiments.

With regard to the various embodiments possible for a derivative of phosphatase WO 92/15316 gives examples of how to modify proteins and polypeptides in order to provide modified substances with an additional net negative charge by derivatisation of their amino groups and/or other basic functional groups with a reagent that prevents protonisation of basic amino groups and/or other basic functional groups or replaces said basic groups by one or more functional groups having a negative charge. The groups to be derived can be histidine and/or lysine residues. The reagent can be chosen from aldehydes, anhydrides, acid chlorides and isothiocyanates. For serum albumin a suitable reagent is cis-aconitate anhydride. Another suitable protein to be modified and linked to phosphatase to form a derivative according to the invention is α-acid glyco-protein.

It is also possible to create a derivative of alkaline phosphatase having optimal phosphatase activity at physiological pH, which derivative is therefore suitable for use in vivo and such a derivative also falls within the scope of the invention.

The subject invention not only covers the derivatives as described above in the various embodiments but also covers a pharmaceutical composition comprising at least one such derivative of phosphatase having phosphatase activity or a vehicle capable of producing such a derivative of phosphatase having phosphatase activity as active component and further comprising a pharmaceutically acceptable carrier.

In particular a pharmaceutical composition, wherein the active component as described i.e. the phosphatase as such, the derivative of phosphatase which is systemically applicable and/or comprises a net negative charge larger than that of the corresponding native phosphatase or a vehicle capable of producing the phosphatase or the derivative thereof having phosphatase activity is embedded in the lipid bilayer of a liposome, preferably in combination with negatively charged membrane constituents is a preferred embodiment of the invention. In such a composition the phosphatase is a phosphatase having phosphatase activity having detoxifying activity for an endotoxin or a derivative thereof.

Use of a phosphatase derivative in any of the embodiments described above as active component for the preparation of a pharmaceutical composition for prophylaxis or therapy of pathology mediated by endotoxin or by a derivative of endotoxin having endotoxic activity is also therefore covered by the subject invention. In particular a pharmaceutical composition comprising a negatively charged and/or systemically applicable derivative of alkaline phosphatase or a vehicle capable of delivering and/or inducing synthesis of the alkaline phosphatase of the derivative in any of the described embodiments forms a preferred embodiment of the invention. A systemically acceptable pharmaceutical composition is preferred.

A method for therapy or prophylaxis of pathology mediated by endotoxin or by a derivative thereof having endotoxic activity comprising administering to a subject a therapeutic amount of such a pharmaceutical composition or any derivative of a phosphatase having phosphatase activity and a pharmaceutically acceptable carrier also falls within the scope of the invention. In particular the subject invention is also directed at a method for preventing occurrence of a pathology mediated by endotoxin or a derivative thereof having endotoxic activity following transplant or transfusion, said method comprising subjecting the material to be transplanted or transfused to treatment before and/or during and/or after transplant or transfusion with one of the following components:

phosphatase as such having detoxifying activity for an endotoxin or for a derivative of endotoxin having endotoxic activity, said phosphatase preferably being alkaline phosphatase, more preferably human alkaline phosphatase;

a derivative of a phosphatase having phosphatase activity according to at least one of the embodiments of the invention as described above;

a vehicle capable of delivering and/or inducing synthesis or phosphatase activity of the phosphatase or the phosphatase derivative having detoxifying activity for an endotoxin or for a derivative of endotoxin having endotoxic activity, said phosphatase preferably being alkaline phosphatase;

a vehicle capable of delivering and/or inducing synthesis or phosphatase activity of a derivative of phosphatase according to the invention as described above, as such or as active component of a pharmaceutical composition. Preferably the pharmaceutical composition has a form rendering the active component capable of entering the blood stream.

To test whether the endotoxin detoxifying mechanism is upregulated in the presence of this bacterial product, human neutrophils were isolated, pre-incubated with endotoxin and assayed for alkaline phosphatase activity. Thus, neutrophils were isolated from normal human volunteers according to standard methods and collected in sterile medium. Neutrophils were not activated during the isolation procedure as assessed by measurements of superoxide anion production by these cells. Subsequently, cells ($0.9 \times 10^7$ cells/ml) were incubated at 37° C. in buffer supplemented with endotoxin (20 pg/ml) or saline. After 30 minutes, alkaline phosphatase activity was assayed in these samples according to standard methods at pH 9.8 with pNPP as substrate. Phosphatase activity was measured with and without levamisole (1 mM) added to the medium. Results show an increase of 335% in neutrophilic alkaline phosphatase activity induced by endotoxin (FIG. 6), which is in accordance with the proposed function of this enzyme.

The invention also covers a pharmaceutical composition comprising at least one of the following components:

a substance for stimulating phosphatase activity, of a phosphatase or a derivative thereof having detoxifying activity for an endotoxin or for a derivative of endotoxin having endotoxic activity, preferably for stimulating alkaline phosphatase activity;

a vehicle capable of delivering and/or inducing synthesis of a substance for stimulating phosphatase activity of a phosphatase or for a derivative thereof having detoxifying activity for an endotoxin or a derivative of an endotoxin having endotoxic activity, preferably for stimulating alkaline phosphatase activity as active component and further comprising a pharmaceutically acceptable carrier, said pharmaceutical composition being systemically applicable.

The invention also covers a pharmaceutical composition comprising at least one of the following components:

a substance for stimulating phosphatase activity, of a phosphatase or a derivative thereof having detoxifying activity for an endotoxin or for a derivative of endotoxin having endotoxic activity, preferably for stimulating alkaline phosphatase activity;

a vehicle capable of delivering and/or inducing synthesis of a substance for stimulating phosphatase activity of a phosphatase or for a derivative thereof having detoxifying activity for an endotoxin or a derivative of an endotoxin having endotoxic activity, preferably for stimulating alkaline phosphatase activity as active component and further comprising a pharmaceutically acceptable carrier in combination with a further active component being a phosphatase as such or a derivative of a phosphatase having phosphatase activity or a vehicle capable of delivering and/or inducing synthesis of said phosphatase and/or said derivative, with the proviso that the pharmaceutical composition does not comprise (alkaline) phosphatase as derivative with collagen and/or demineralized bone, i.e. does not comprise a pharmaceutical composition as described by Beersten et al. for osteogenisis in situ of the desired bone formation. A pharmaceutical composition comprising a derivative of phosphatase having a net negative charge in comparison to the corresponding native phosphatase or a vehicle capable of delivering and/or inducing synthesis of said derivative as one of the active components in combination with the substance or substance producing vehicle, said substance being capable of stimulating phosphatase activity is included within the scope of invention. The activating effect of the natural detoxifying action of phosphatase, preferably endogenous phosphatase, in particular of alkaline phosphatase can thus be stimulated further and provide a means of defense against the negative pathological symptoms caused by endotoxins or derivatives thereof having endotoxic activity. In particular the substance for stimulating phosphatase activity, preferably for stimulating alkaline phosphatase activity can be selected from one or more of the following: an endotoxin, a substance having endotoxic activity, granulocyte colony stimulating factor (G-CSF), retinoic acid, a glucocorticoid and any other cytokines or substances known to stimulate phosphatase activity (ref. 13, 29 and 30).

The subject invention also covers the use of any of the aforementioned active components for stimulating phosphatase activity as active component for preparation of a pharmaceutical composition for prophylaxis or therapy of pathology mediated by endotoxin or a derivative of endotoxin having endotoxic activity. It also covers the use of said active component for stimulating phosphatase activity in combination with phosphatase as such or any derivative of phosphatase having phosphatase activity or any vehicle capable of delivering and/or inducing the synthesis of said derivative for preparation of such a pharmaceutical composition.

A method for preventing occurrence of a pathology mediated by endotoxin or a derivative thereof having endotoxic activity, said method comprising stimulating phosphatase activity in particular by increasing endogenous alkaline phosphatase activity, for example by increasing production thereof in a subject by administering at least one of the aforementioned components as such or as active component of a pharmaceutical composition to the subject also falls within the scope of the invention. As does a method for preventing occurrence of a pathology mediated by endotoxin or a derivative thereof having endotoxic activity following transplant or transfusion, said method comprising subjecting the material to be transplanted or transfused to treatment stimulating phosphatase activity, in particular by increasing the activity of endogenous alkaline phosphatase, for example by increasing production thereof of said material by administering at least one of the following components:

a substance for stimulating phosphatase activity, in particular by increasing the activity of endogenous phosphatase or a derivative thereof having detoxifying activity for an endotoxin or for a derivative of an endotoxin having endotoxic activity;

a vehicle capable of delivering and/or inducing synthesis of the substance for stimulating phosphatase activity as such or as active component of a pharmaceutical composition to the subject. A suitable embodiment of this aspect of the invention can be found in a method for increasing the presence of alkaline phosphatase, preferably endogenous alkaline phosphatase in the body, the tissue or the body fluid of an animal or human comprising application of at least one of the aforementioned components for stimulating phosphatase activity as such or as active component of a composition.

In summary from the above described experiments it can be concluded that enzyme preparations based upon alkaline phosphatase activity are able to dephosphorylate endotoxin thereby attenuating the toxicity of this molecule in vitro and in vivo. The physiological activity of this enzyme is most prominent when associated with negatively charged residues which provide the proper micro environmental conditions. Furthermore, alkaline phosphatase activity can be upregulated in cells of the host-defence system, providing a natural barrier against endotoxin.

The subject invention also covers a pharmaceutical composition comprising at least one of the following components:

phosphatase as such having phosphatase activity in vivo in or on bone, said phosphatase preferably being alkaline phosphatase, more preferably human (alkaline) phosphatase and preferably being recombinant phosphatase;

a systemically acceptable derivative of the alkaline phosphatase, said derivative having said phosphatase activity in vivo in or on bone and/or a derivative;

a vehicle capable of delivering and/or inducing synthesis or phosphatase activity of said phosphatase as such an/or said derivative and/or the derivative, as active component in vivo and further comprising a pharmaceutically acceptable carrier. In vivo in this context implies in a macro environment having physiological pH, i.e. a pH of 7–8. A suitable embodiment of such a pharmaceutical composition comprises the active component embedded in the lipid bilayer of a liposome, preferably in combination with negatively charged membrane constituents.

The subject invention further comprises use of at least one of the following components:

a phosphatase as such having phosphatase activity in vivo, preferably in or on bone, more preferably alkaline phosphatase and more preferably human alkaline phosphatase and preferably being recombinant phosphatase;

a derivative of alkaline phosphatase having phosphatase activity in vivo, preferably in or on bone;

a vehicle capable of delivering and/or inducing synthesis of said phosphatase as such and/or said derivative as active component in vivo for preparation of a pharmaceutical composition for prophylaxis or therapy of metabolic bone diseases, such as osteoporosis and osteomalacia.

Use of at least one of the following components:

phosphatase as such having phosphatase activity in vivo, preferably in or on bone more preferably alkaline phosphatase and more preferably human (alkaline) phosphatase and preferably being recombinant phosphatase, a derivative of phosphatase having phosphatase activity in vivo preferably in or on bone, said derivative being a systemically acceptable derivative of alkaline phosphatase having phosphatase activity in vivo and/or a derivative, preferably with increased net negative charge in comparison to the corresponding native phosphatase;

a vehicle capable of delivering and/or inducing synthesis or phosphatase activity of said phosphatase as such and/or said derivative, as active component for preparation of a pharmaceutical composition for prophylaxis or therapy of pathology requiring increased bone formation such as stimulating mending of broken bone and prophylaxis or therapy of metabolic bone disorders, such as osteoporosis and osteomalacia also falls within the scope of invention.

Also a pharmaceutical composition comprising at least one of the following components:

a substance for stimulating phosphatase activity, preferably of an endogenous phosphatase or a derivative thereof, said phosphatase or derivative having detoxifying activity for an endotoxin and/or for a derivative of endotoxin having endotoxic activity and/or said phosphatase or derivative having phosphatase activity in vivo, in particular in or on bone, said substance preferably being a substance for stimulating alkaline phosphatase activity, more preferably human (alkaline) phosphatase;

a vehicle capable of delivering and/or inducing synthesis of said substance for stimulating phosphatase activity, more preferably human (alkaline) phosphatase activity, as active component and further comprising a pharmaceutically acceptable carrier, said pharmaceutical composition being systemically applicable falls within the scope of the invention. The invention is also directed at a pharmaceutical composition comprising at least one of the following components:

a substance for stimulating phosphatase activity, preferably of an endogenous phosphatase or a derivative thereof, said phosphatase or derivative having detoxifying activity for an endotoxin and/or for a derivative of endotoxin having endotoxic activity and/or said phosphatase or derivative having phosphatase activity in vivo, in particular in or on bone, said substance preferably being a substance for stimulating alkaline phosphatase activity, more preferably human (alkaline) phosphatase;

a vehicle capable of delivering and/or inducing synthesis of said substance for stimulating phosphatase activity, more preferably human (alkaline) phosphatase activity, as active component and further comprising a pharmaceutically acceptable carrier, in combination with at least one of the active components, a phosphatase as such having phosphatase activity in vivo, preferably in or on bone, more preferably alkaline phosphatase and more preferably human alkaline phosphatase and preferably being recombinant phosphatase;

a derivative of (alkaline) phosphatase having phosphatase activity in vivo, preferably in or on bone;

a vehicle capable of delivering and/or inducing synthesis of said phosphatase as such and/or said derivative as active component in vivo or at least one of the following components;
- a phosphatase as such having detoxifying activity for an endotoxin and/or for a derivative thereof having endotoxic activity, said phosphatase preferably being alkaline phosphatase, more preferably human alkaline phosphatase and said phosphatase preferably being recombinant phosphatase;
- a derivative of the phosphatase having phosphatase activity for an endotoxin and/or for a derivative thereof, having endotoxic activity, said phosphatase preferably being alkaline phosphatase, more preferably human alkaline phosphatase and said phosphatase preferably being recombinant phosphatase, said derivative preferably being a systemically acceptable derivative of a phosphatase and/or being a derivative preferably having an increased net negative charge in comparison to the corresponding native phosphatase;
- a vehicle capable of delivering and/or inducing synthesis or phosphatase activity of said phosphatase as such or the derivative of phosphatase as active component.

The substance for stimulating alkaline phosphatase activity can be suitably selected from one or more of the following: an endotoxin, a substance having endotoxic activity, granulocyte colony stimulating factor (G-CSF), retinoic acid, a glucocorticoid. Any other such substances known to a person skilled in the art can also be used to obtain the desired stimulation of (alkaline) phosphatase activity according to the invention.

In a pharmaceutical composition comprising a substance for stimulating phosphatase activity or a vehicle capable of delivering such a substance as described above, the further active components can be any of the components;
- a phosphatase as such having detoxifying activity for an endotoxin and/or for derivatives thereof having endotoxic activity, said phosphatase preferably being alkaline phosphatase, more preferably human alkaline phosphatase and said phosphatase preferably being recombinant phosphatase;
- a derivative of the phosphatase, said derivative having the phosphatase activity and said derivative being systemically acceptable preferably having an increased negative charge in comparison to the corresponding native phosphatase;
- a vehicle capable or delivering and/or inducing synthesis of phosphatase activity of said phosphatase as such and/or said derivative;
- phosphatase as such having phosphatase activity in vivo in or on bone, said phosphatase preferably being alkaline phosphatase, more preferably humen (alkaline) phosphatase and preferably being recombinant phosphatase;
- a systemically acceptable derivative of the alkaline phosphatase, said derivative having said phosphatase activity in vivo in or on bone and/or a derivative;
- a vehicle capable of delivering and/or inducing synthesis or phosphatase activity of said phosphatase as such and/or said derivative.

In any of the embodiments disclosed the pharmaceutical composition can comprise the active component embedded in the liquid bilayer of a liposome, preferably in combination with negatively charged membrain constituents. Preferably a pharmaceutical composition will be systemically acceptable.

The subject invention is also directed at use of at least one of the active components of a pharmaceutical composition comprising a substance for stimulating phosphatase activity or a vehicle for delivering and/or inducing synthesis of said substance as active component for preparation of a pharmaceutical composition for prophylaxis or therapy of pathology mediated by an endotoxin and/or by a derivative of endotoxin having endotoxic activity. Also the use of at least one of the just mentioned active components as active component for preparation of a pharmaceutical composition for prophylaxis or therapy of metabolic bone diseases, such as osteoporosis and osteomalacia falls within the scope of the invention. In addition, use of at least one of the active components of a pharmaceutical composition as described herein in combination with at least one of the active components of a pharmaceutical composition having a substance for stimulating phosphatase activity, a vehicle capable of delivering and/or inducing synthesis of a substance for stimulating phosphatase activity and a pharmaceutically acceptable carrier as active component for preparation of a pharmaceutical composition for prophylaxis or therapy of pathology requiring increased bone formation such as stimulating mending of broken bones and prophylaxis or therapy of metabolic bone diseases such as osteoporosis and osteomalacia falls within the scope of the invention. Also the invention is directed at a method for prophylaxis or therapy of metabolic bone disease such as osteoporosis and osteomalacia requiring increased bone formation, said method comprising application of at least one of a phosphatase, a derivative of an alkaline phosphatase having phosphatase activity in vivo and a vehicle to the subject to be treated. A method for prophylaxis or therapy of pathology requiring increased bone formation such as stimulating mending of broken bone and prophylaxis or therapy of metabolic bone disease such as osteoporosis and osteomalacia, said method comprising administering at least one of the active components of a pharmaceutical composition as described herein as such or as active component of a composition to the subject to be treated as well as a method of treatment of pathology associated with rapid bone formation such as osteosarcoma, said method comprising decreasing or inhibiting alkaline phosphatase activity, preferably in a target specific manner, i.e. at the location where said pathology occurs forms part of the invention. In all the methods disclosed the active components can be systemically applicable. In addition to the previously mentioned pharmaceutical compositions a pharmaceutical composition comprising at least one substance capable of decreasing or inhibiting phosphatase activity and/or the concentration of phosphatase in particular alkaline phosphatase (activity), said substance preferably being targeted to act at a location where undesired bone formation is to be prevented is covered by the invention.

REFERENCES

Figure 1A:
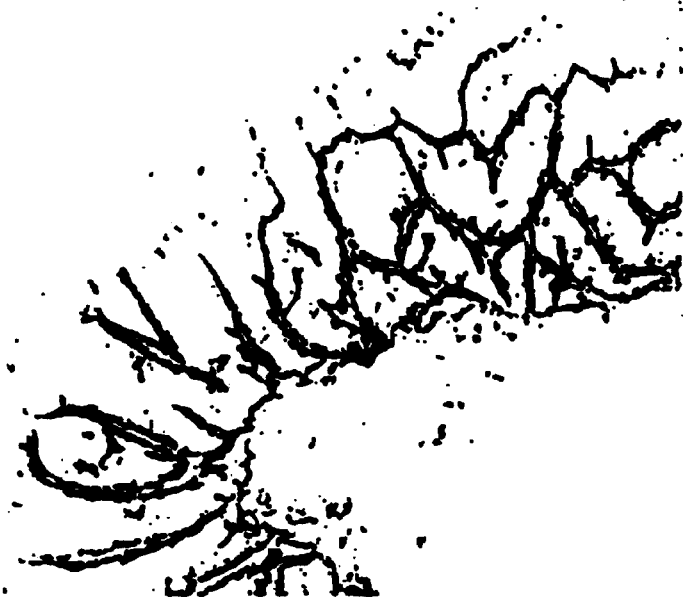
FIG. 1 Alkaline phosphatase activity in cryostat sections of rat intestine (A) and kidney (B) as demonstrated at pH 9.0 with the substrate β-glycerophosphate. FIG. C and D show phosphatase activity in sections of intestine (C) and kidney (D) as demonstrated with endotoxin as substrate at pH 7.4. Significant dephosphorylation of endotoxin is found along intestinal crypts (FIG. C) and in tubular brushborders of the kidney (FIG. D), corresponding with the localization of alkaline phosphatase activity (FIG. A & B). Furthermore, in intestinal sections this activity is reduced by addition of L-phenyl-alanine (FIG. E), whereas endotoxin dephosphorylation in kidney sections is completely inhibited by levamisole (FIG. F). Abbreviation: m=medulla. Magnification: 35× (A,B), 140× (C,E) and 56× (D,F).
Figure 1B:
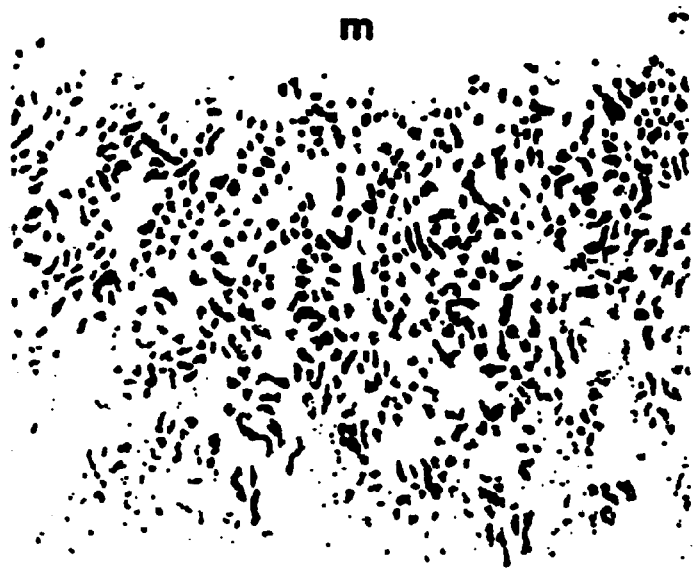
Figure 1C:
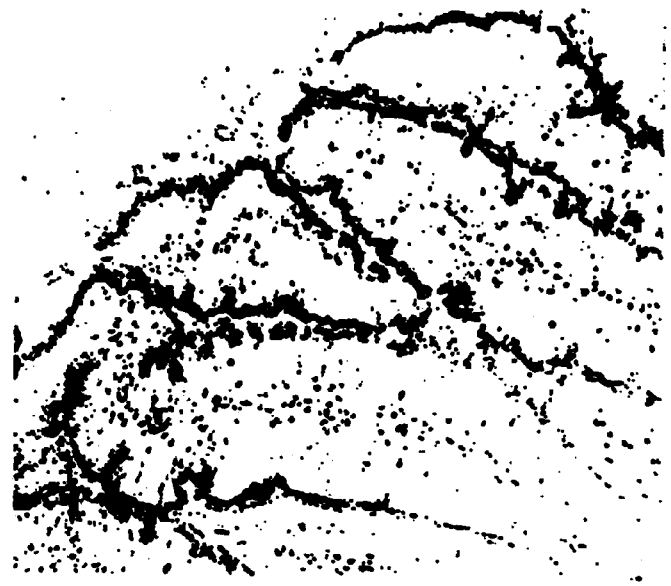
Figure 1D:
Figure 1E:
Figure 1F:
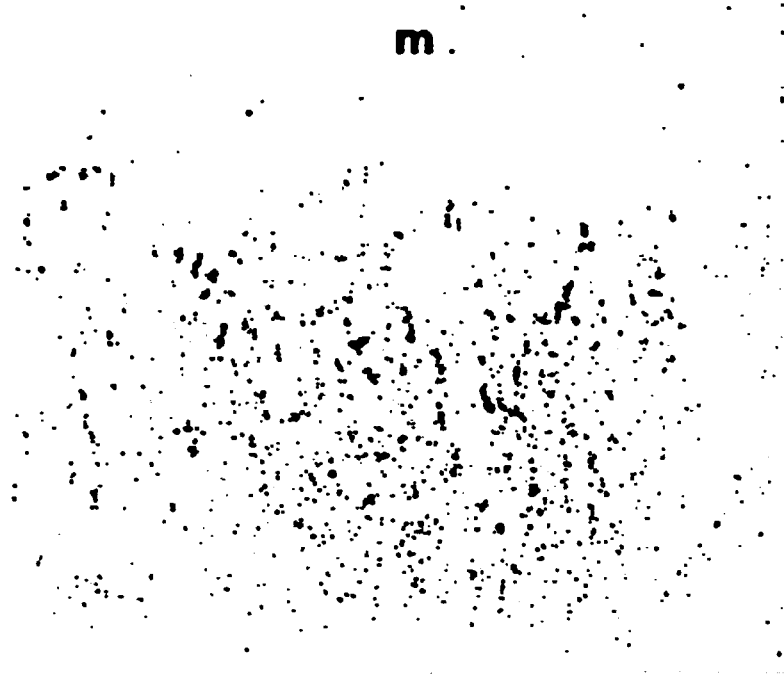
Figure 2:
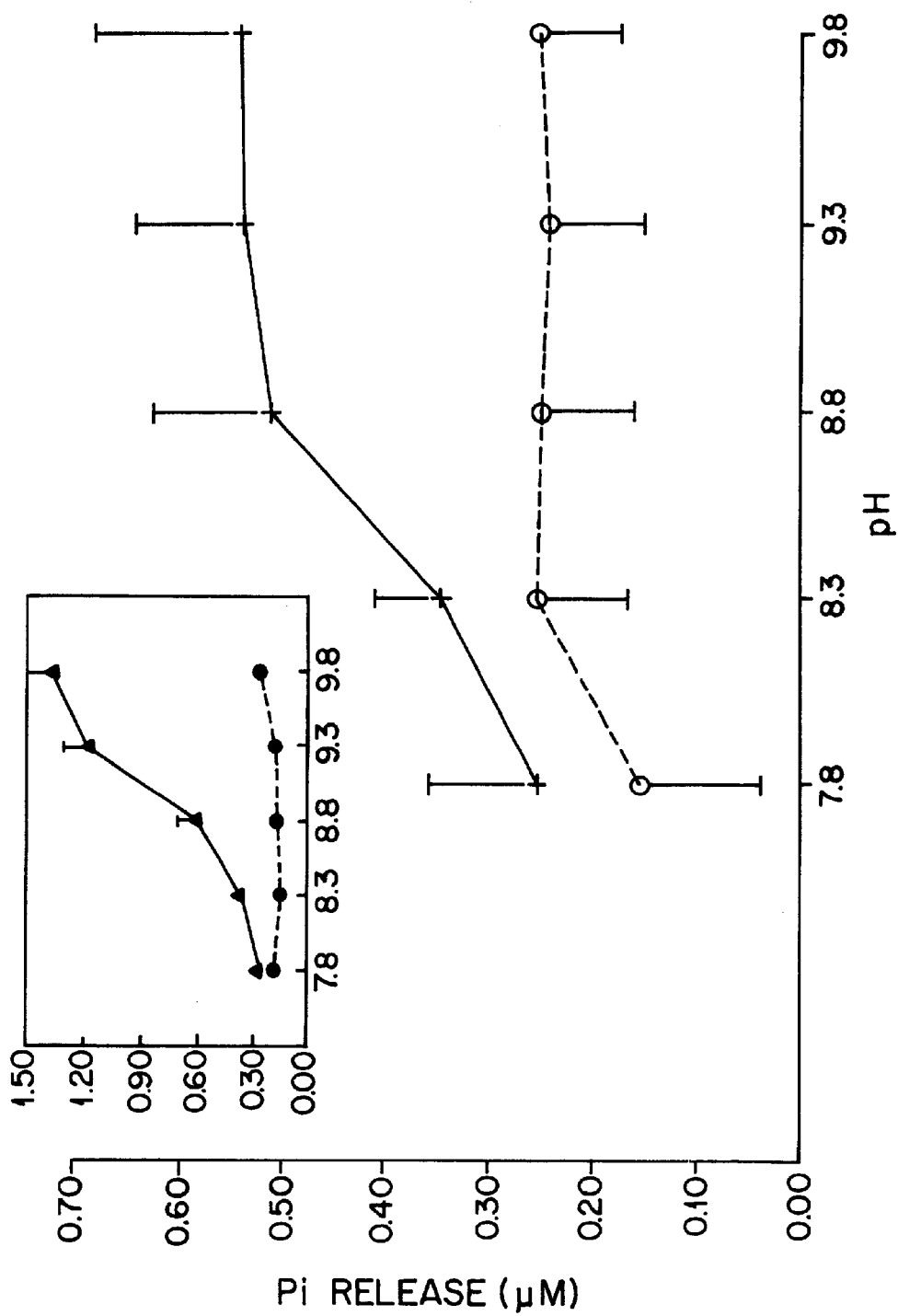
FIG. 2 Phosphatase activity, expressed as inorganic phosphate (Pi) release per hour, in suspensions of tubular brushborders at different pH levels with endotoxin as substrate. Phosphatase activity with the substrate paranitrophenolphosphate (pNPP) is shown in the upper left corner. Tubular brushborder fragments were isolated from the cortex of PVG rat kidneys and added to 250 µl 2-amino-2-methyl-1,3-propanediol buffer at different pH levels, containing E. coli endotoxin (1.25 mg/ml) or pNPP (0.5 mg/ml). 2 mM $MgCl_2$ was added immediately before incubation. Dashed lines indicate phosphatase activity in the presence of levamisole (0.2 mM). After one hour incubation at 37° C., inorganic phosphate concentrations were assessed as described previously (ref. 29). Results are expressed as arithmetic means (±SD) of 6 assays, each assay was performed in duplicate. Results show that maximal dephosphorylation of endotoxin occurs at pH 8.8, whereas dephosphorylation of pNPP shows a steady increase to pH 9.8.
Figure 3A:
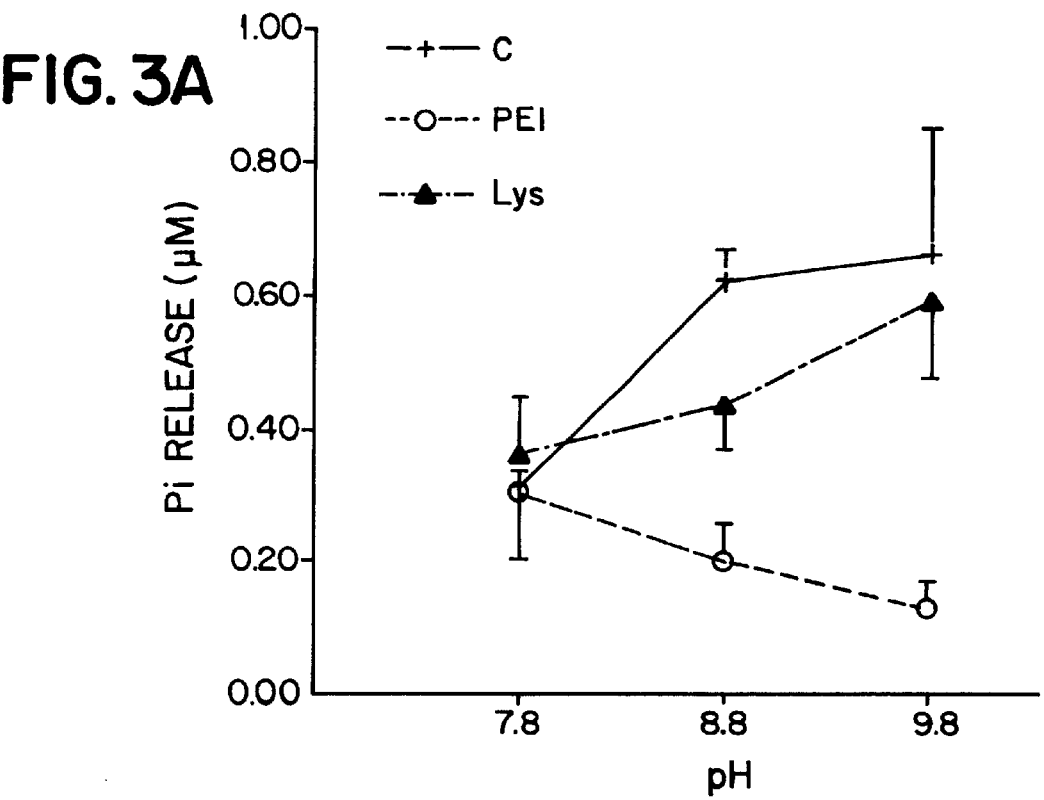
FIG. 3 Phosphatase activity, expressed as phosphate (Pi) release per hour, in suspensions of tubular brushborders at different pH levels with endotoxin (FIG. A) or PNPP (FIG. B) as the substrate. Substrates were preincubated for 30 minutes with either 0.5% poly-ethyleneimine (PEI), 0.75% poly-L-Lysin (Lys) or distilled water (C). Subsequently, incubations were carried out as described at FIG. 2. Results are expressed as the arithmetic means of 4 assays, each assay was performed in duplicate (±SD).
Figure 3B:
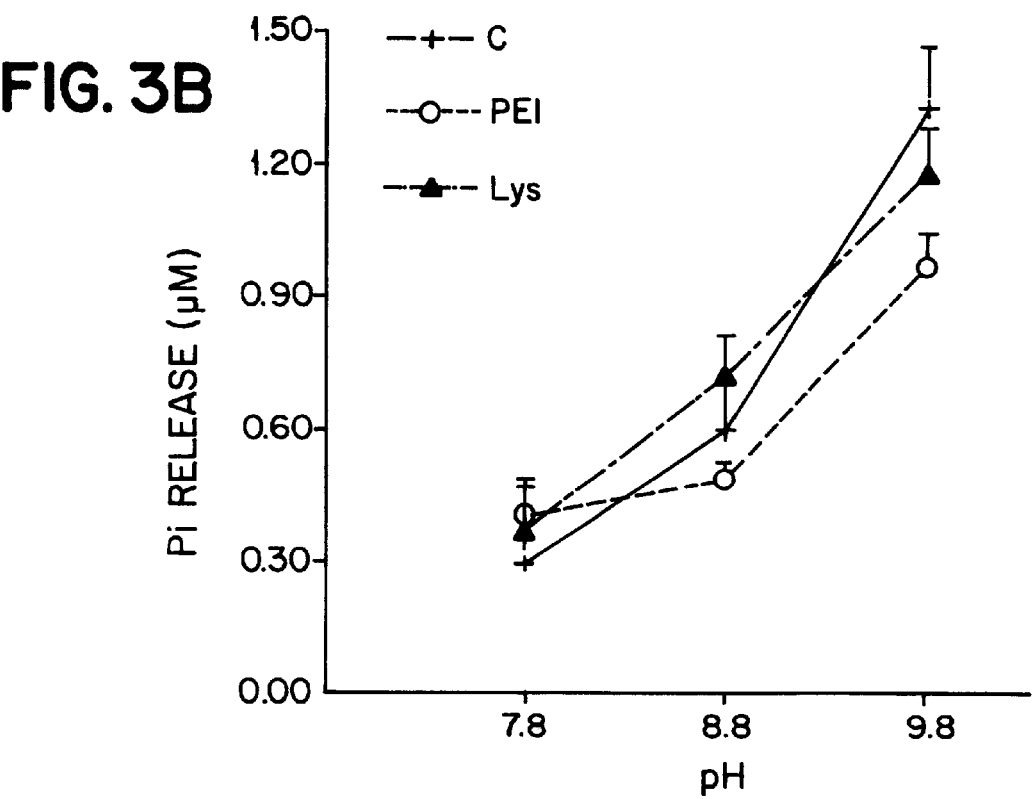
Figure 4:
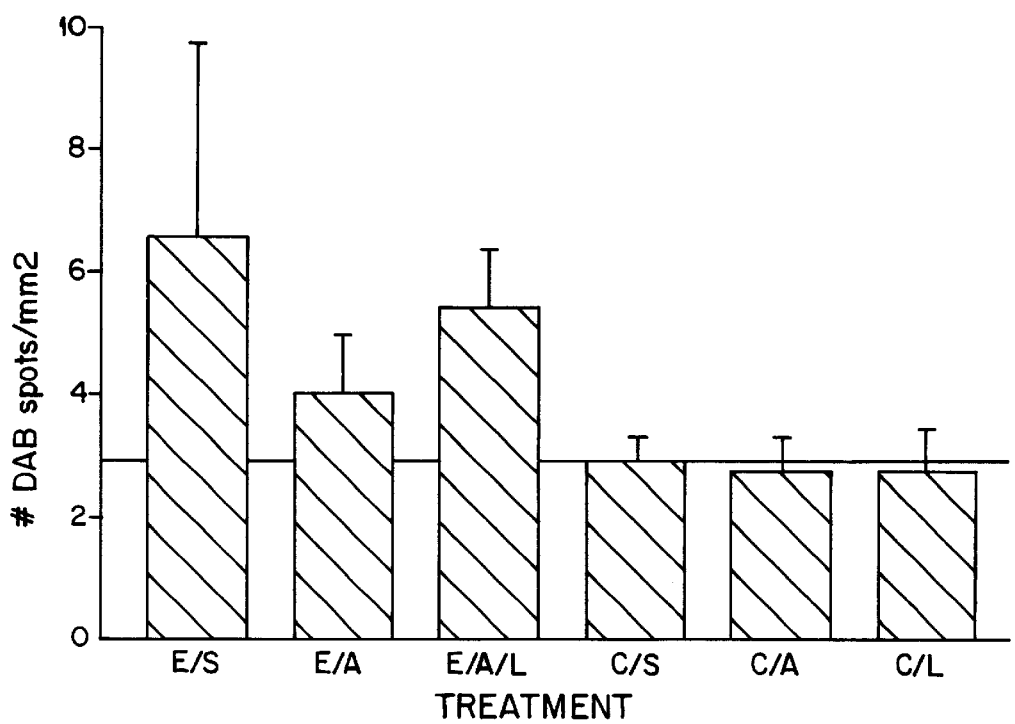
FIG. 4 To assess endotoxin toxicity in vivo, a localized Shwartzman-reaction (ref. 16) was elicited in the skin of PVG rats at different locations on the back. Prior to injection, all media were incubated (1 hour, 37° C.) with 6 µg tubular brushborder fragments containing alkaline phosphatase activity (A), or with 0.9% saline (S). When indicated, the alkaline phosphatase inhibitor levamisole (L) was added (final concentration 1.0 mM). Two hours after the intradermal injections, dermal sites were analyzed for influx of oxygen free radical producing cells, demonstrated histochemically with 3,3'-diaminobenzidine (DAB) at the light-microscopical level[17]. Each test was performed in duplicate on the same rat and results are expressed as the arithmetic mean (±SD) of 6 rats.
Figure 5:
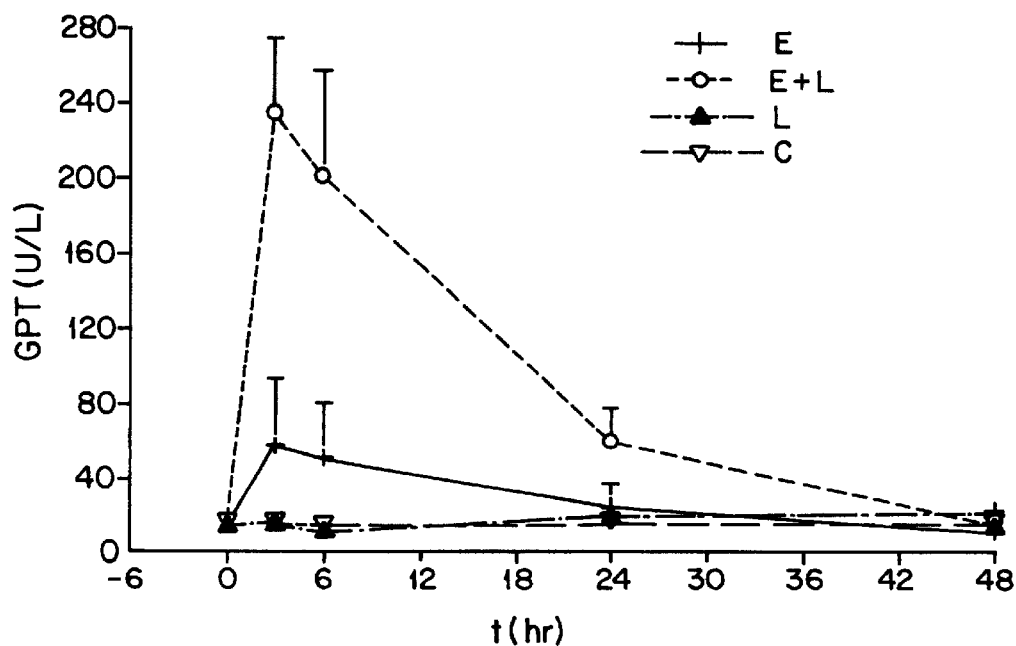
FIG. 5 Effect of eridotoxin upon serum levels of glutamate-pyruvate transaminase (GPT) activity, which reflects damage of liver cells, in PVG rats. Part of the animals were pre-treated with levamisole (L; 10 mg/kg b.w.) at t=−24 and −1 hr. At t=0 rats received either 0.5 mg endotoxin from E. coli (E) intravenously or 0.5 ml saline. Results are expressed as arithmetic means (±SD of 4 rats) per group.
Figure 6:
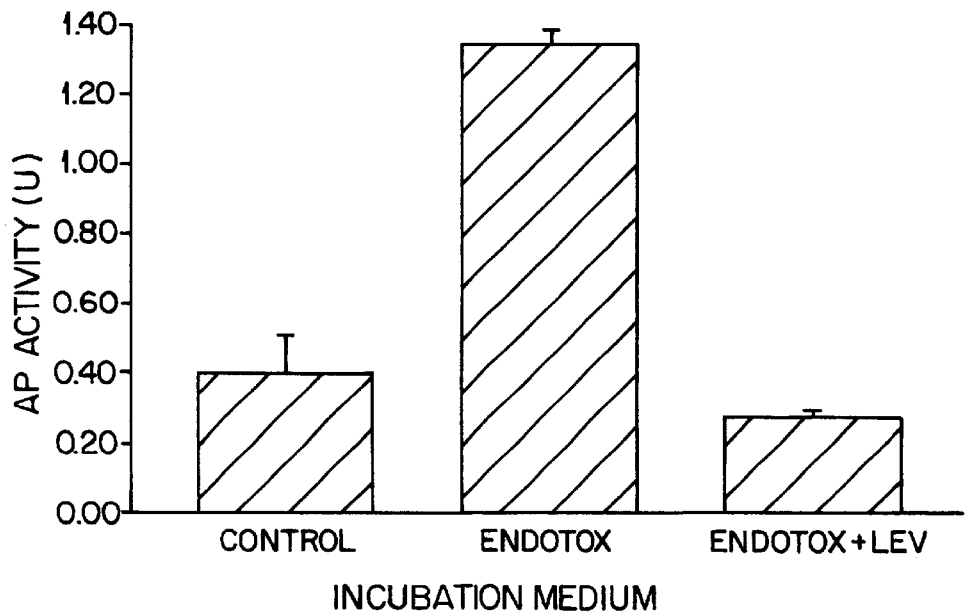
FIG. 6 Effect of endotoxin upon alkaline phosphatase (AP) activity of human neutrophils. Neutrophils were isolated from whole blood according to standard procedures and incubated in 0.9% saline with or without endotoxin from E. coli (20 pg/ml) for 30 minutes at 37° C. Subsequently, phosphatase activity of these cells was measured, using paranitrophenol phosphate as substrate at pH 9.8. Levamisole (1 mM) was added to confirm the involvement of alkaline phosphatase in phosphate release.
Figure 7A:
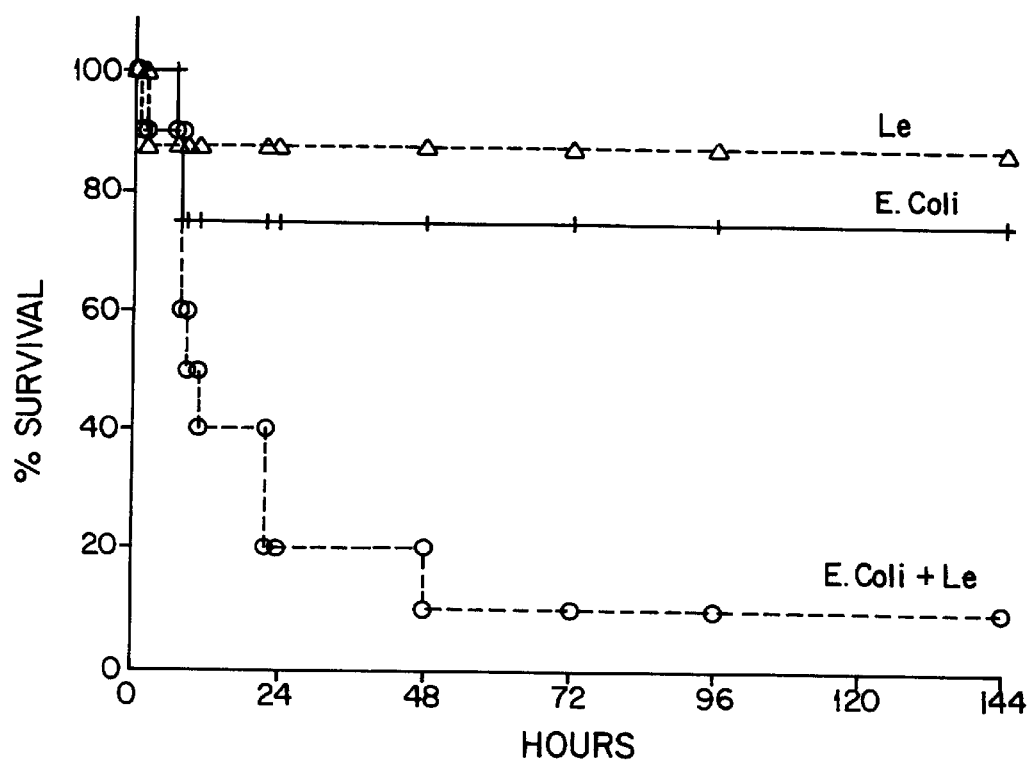
FIG. 7A illustrates the percentage of survival of rats after injection of E. coli (solid line), Levamisole (Le) (dashed line with triangles) or both (dashed line with circles) along the X-axis against time in hours along the Y-axis.
Figure 7B:
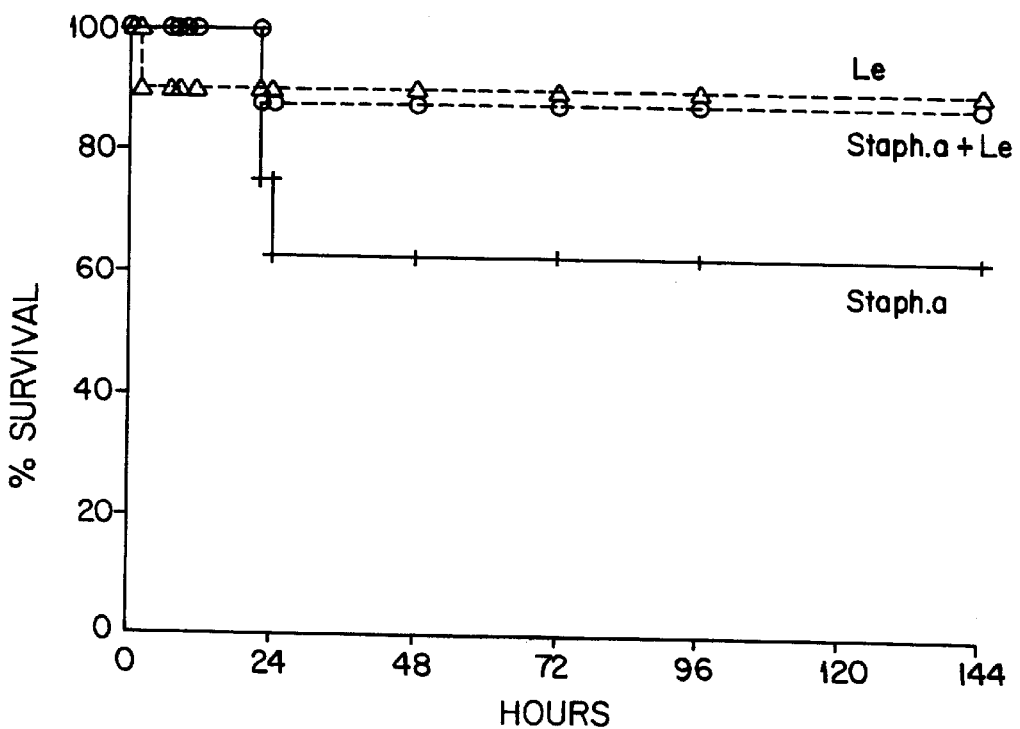
FIG. 7B illustrates the percentage of survival of rats after injection of Staphylococcus aureus (solid line), Levamisole (Le) (dashed line with triangles) or both (dashed line with circles).
Figure 8:
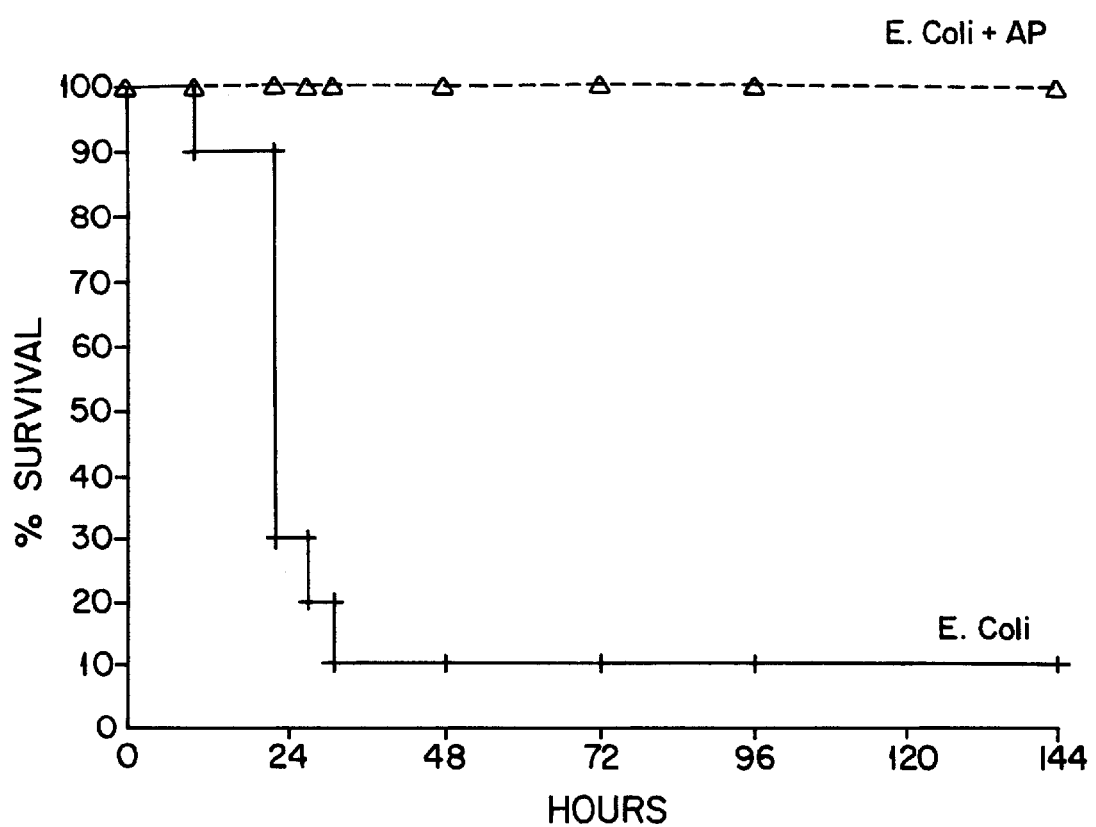
FIG. 8 illustrates the survival of mice after injection of E. coli with alkaline phosphatase treatment (dashed line) and without alkaline phosphatase (solid line).

1. Gajewski, J. L. et al. Transplantation 50, 244–249 (1990).
2. Lau, A. S. & Williams, B. R. J. Exp. Pathol. 5, 111–22 (1990).
3. Rietschel, E. Th. et al. in Cellular and Molecular Aspects of Endotoxin Reactions (eds Nowothy, A., Spitzer, J. J. & Ziegler, E. J.) 15–32 (Elsevier Science Publishers B. V., Amsterdam, 1990).
4. Peterson, A. A. & Munford, R. S. Infection and Immunity 55, 974–978 (1987).
5. Parrillo, J. E. et al. Ann. Intern. Med. 113, 227–242 (1990).
6. Ohlsson, K. et al. Nature 348, 550–552 (1990).
7. MacSween, R. N. M., Whaley, K., (eds.): Muir's Textbook of Pathology, 13th edition, Edward Arnold, London, Melbourne Auckland, chapter 8, p. 279–337 (1992).
8. MacSween, R. N. M., Whaley, J. (eds).: Muir's Textbook of Pathology, 13th edition, Edward Arnold, London, Melbourne Auckland, chapter 3, p. 73–111 (1992).
9. Skarnes, R. C. in Handbook of Endotoxin. Vol. 3: Cellular Biology of Endotoxins (ed. Berry, L. J.), 56–81 (Elsevier Science Publishers B.V., Amsterdam, 1985).
10. Johnson, K. J. et al. Am.J.Pathol. 88: 559–574, 1977.
11. Matsuura, S., Kishi, F. & Kajii, T. Biochem. and Biophys. Res. Comm. 168, 993–1000 (1990).
12. McComb, R. B., Bowers Jr. G. N. & Posen S. in Alkaline Phosphatase 865–902 (Plenum Press, New York, London, 1979).
13. Chikkappa, G. Exp. Hematol. 20, 388–390 (1992).
14. Kaplan, M. M. Hepatology 6, 526–528 (1986).
15. Stryer L., in Biochemistry (3rd ed.), p.275–277 (W. H. Freeman and Company, New York, 1988).
16. McComb, R. B., Bowers, G. N., Posen, S, in Alkaline Phosphatase, p.64–67 (Plenum Press, New York, London, 1979).
17. McComb, R. B., Bowers, G. N., Posen, S., in Alkaline Phosphatase. p.589–590 (Plenum Press, New York, London, 1979).
18. Chikkappa, G., Exp. Hematol. 20, 388–390, 1992.
19. Ashley, D. J. B., in Evans' Histological Appearances of Tumours (third edition), p.117–118 (Churchill Livingstone, Edinburgh, London, N.Y., 1978).
20. Goor van, H., Gerrits, P. O. & Hardonk, M. J. J. Histochem. and Cytochem. 37, 399–403 (1989).
21. Wachstein, M. & Meisel, E. Am. J. Clin. Pathol. 27, 13–23 (1957).
22. Brock, D. J. Lancet ii, 941–943 (1983).
23. Chandrarajan J., Klein L., Anal.Biochem. 72, 407–412 (1976).
24. Somlyo, B. et al. Int. J. Immunopharmacol. 14, 131–142 (1992).
25. Levin, J., Bang. F. B., Bull. Johns Hopkins Hosp. 115, 265–274 (1964).
26. Brozna, J. P. Semin. Thromb. Hemost. 16, 326–332 (1990).
27. Poelstra, K., Hardonk, M. J., Koudstaal, J. & Bakker, W. W. Kidney Int. 37, 1500–1508 (1990).
28. Scholtens, H. B., Hardonk, M. J., Meijer, D. K. F., Liver, 2, 1–13, (1982).
29. Rambaldi, A. et al. in Blood, Vol. 76, No. 12 (December 15), 1990: p. 2565–2571.
30. Yuo, A. et al., in Blood, Vol. 70, No. 2 (August), 1987: p.404–411.

31. Clubb, J. S., Neale, F. C., & Posen S. *J. Lab. & Clin. Med.* 66, 493–507 (1965).
32. Bos van den, T., & Beertsen, W. *J. Biomed. Mat. Res.* in press (1994).
33. Ecarot, B., et al. *J. Bone Miner. Res.* 7, 523–530 (1992).
34. McComb, R. B., Bowers, G. N., & Posen. S. in *Alkaline phosphatase.* Ch. 9 Clinical utilization of alklaline phosphatase measurements. p525–786 (Plenum Press, New York, London, 1979).
35. Ross, M. H. *J. Nutr.* 97, 565 (1969).
36. Kaplow, L. S. *Crit. Rev. Clin. Lab. Sci.* 2, 243, (1971).
37. Mueller, M., Kappas. A., & Damgaard, E. *J. Clin. Invest.* 43, 1905 (1964).

What is claimed is:

1. A method of dephosphorylating an endotoxin comprising:

administering to a mammal a composition comprising a first alkaline phosphatase having dephosphorylating activity in vivo in an amount sufficient to dephosphorylate endotoxin produced by bacteria in vivo, optionally, a vehicle comprising a second alkaline phosphatase which may be identical to said first alkaline phosphatase, having dephosphorylating activity in vivo, wherein said second alkaline phosphatase is obtained from an isolated, purified recombinant DNA sequence encoding an alkaline phosphatase isozyme having dephosphorylating activity in vivo and;

a pharmaceutically acceptable carrier, thereby dephosphorylating the endotoxin.

2. The method according to claim 1, wherein at least one member of the group consisting of said first alkaline phosphatase and said second alkaline phosphatase comprises a human alkaline phosphatase.

3. The method according to claim 2, wherein said human alkaline phosphatase comprises human placental alkaline phosphatase.

4. The method according to claim 1, wherein said vehicle comprises liposomes.

5. The method according to claim 1, wherein said composition is administered by injection.

* * * * *